(12) United States Patent
Stimpson et al.

(10) Patent No.: US 7,273,589 B2
(45) Date of Patent: Sep. 25, 2007

(54) SAMPLES DELIVERING DEVICE, METHOD OF MANUFACTURING SAMPLES APPLICATOR, METHOD OF DELIVERING SAMPLES, AND BASE ACTIVATION DEVICE

(75) Inventors: Donald I. Stimpson, Bennett, CO (US); Hideji Tajima, Pleasanton, CA (US)

(73) Assignee: PSS Bio Instruments, Inc., Livermore, CA (US)

( * ) Notice: Subject to any disclaimer, the term of this patent is extended or adjusted under 35 U.S.C. 154(b) by 567 days.

(21) Appl. No.: 10/445,646

(22) Filed: May 27, 2003

(65) Prior Publication Data
US 2004/0037750 A1 Feb. 26, 2004

Related U.S. Application Data

(60) Provisional application No. 60/383,731, filed on May 28, 2002.

(51) Int. Cl.
*B01L 3/02* (2006.01)
*G01N 35/00* (2006.01)
(52) U.S. Cl. ............... 422/100; 422/63; 422/68.1; 436/44; 436/180
(58) Field of Classification Search ........... 422/100, 422/63, 65–66, 68.1; 436/180, 44
See application file for complete search history.

(56) References Cited

U.S. PATENT DOCUMENTS

| 5,807,522 | A | 9/1998 | Brown et al. |
| 6,101,946 | A * | 8/2000 | Martinsky ............ 101/494 |
| 6,221,653 | B1 | 4/2001 | Caren et al. |
| 6,551,557 | B1 * | 4/2003 | Rose et al. ............ 422/100 |

(Continued)

FOREIGN PATENT DOCUMENTS

JP 10-503841 4/1998

(Continued)

*Primary Examiner*—Brian R. Gordon
(74) *Attorney, Agent, or Firm*—Haynes and Boone, LLP (57) ABSTRACT

The present invention relates to a samples delivering device, a method of manufacturing a samples applicator, a method of delivering samples, and a base activation device which can handle a plurality of various samples, efficiently and promptly. The invention is constructed so as to have: one or more sets of vessels capable of accommodating fluids containing predetermined samples to be delivered to a base or one or more sets of vessels, a samples supply section having a samples applicator, wherein two or more retention tips capable of retaining a small quantity of fluids by being dipped in each of the fluids accommodated in the vessels are arranged according to the vessels, and a transfer means for relatively moving between the base and the one or more sets of vessels, and the applicator.

17 Claims, 9 Drawing Sheets

U.S. PATENT DOCUMENTS

| | | |
|---|---|---|
| 6,627,446 B1 * | 9/2003 | Roach et al. .................. 436/43 |
| 6,629,626 B1 * | 10/2003 | Horsman et al. ............ 222/420 |
| 2001/0005489 A1 * | 6/2001 | Roach et al. .................. 422/99 |
| 2002/0110900 A1 * | 8/2002 | Jovanovich et al. ...... 435/286.4 |
| 2003/0032198 A1 * | 2/2003 | Lugmair et al. ............. 436/180 |
| 2003/0062265 A1 * | 4/2003 | King et al. .................. 204/453 |
| 2003/0086828 A1 * | 5/2003 | Chiou et al. ................. 422/100 |
| 2003/0124734 A1 * | 7/2003 | Dannoux ..................... 436/180 |
| 2003/0175163 A1 * | 9/2003 | Shvets et al. ................ 422/100 |
| 2003/0215957 A1 * | 11/2003 | Lemmo et al. .............. 436/180 |
| 2003/0228241 A1 * | 12/2003 | Legge .......................... 422/100 |
| 2004/0033554 A1 * | 2/2004 | Powers ........................ 435/29 |
| 2004/0071603 A1 * | 4/2004 | Pinkel et al. ................. 422/100 |
| 2004/0072365 A1 * | 4/2004 | Rose et al. ................... 436/180 |
| 2004/0096359 A1 * | 5/2004 | Sarrut et al. .................. 422/63 |
| 2005/0036920 A1 * | 2/2005 | Gilbert ......................... 422/100 |
| 2005/0079105 A1 * | 4/2005 | Hunter et al. ................ 422/100 |
| 2005/0130318 A1 * | 6/2005 | Vann et al. ................... 436/180 |
| 2005/0148091 A1 * | 7/2005 | Kitaguchi et al. ........... 436/164 |
| 2005/0169808 A1 * | 8/2005 | Pinkel et al. ................. 422/100 |

FOREIGN PATENT DOCUMENTS

JP              11-187900         7/1999

* cited by examiner

SAMPLES DELIVERING DEVICE, METHOD OF MANUFACTURING SAMPLES APPLICATOR, METHOD OF DELIVERING SAMPLES, AND BASE ACTIVATION DEVICE

CROSS REFERENCE TO RELATED APPLICATION

This application claims priority to U.S. provisional patent application No. 60/383,731, filed on May 28, 2002.

FIELD OF THE INVENTION

The present invention relates to a samples delivering device, a method of manufacturing a samples applicator, a method of delivering samples, and a base activation device. Particularly, the present invention relates to a samples delivering device, a method of manufacturing a samples applicator, a method of delivering samples, and a base activation device which enable extraction and transfer of many various samples. The present invention relates to all manner of fields, for example, in which arrays arranged with materials such as nucleic acids, proteins or sugars are prepared, a large number of various samples are mixed for combinatorial chemistry, or standard immunoassay is executed, by using a multi-well plate format.

BACKGROUND OF THE INVENTION

Currently, the phenomenal increase in the use of high throughput screening and genomic/proteomic arrays has brought about the necessity for manipulation of large numbers of different samples. In the case of arrays, thousands of different DNA samples are often "spotted" onto a support material. In general, the task is to pick up a small volume of liquid from a vessel and apply the volume of liquid to a surface, or disperse and mix the volume of liquid in another liquid containing vessel.

As the technology currently available for carrying out such tasks, the method and apparatus for forming microarrays of biological samples on a support are disclosed (Japanese laid-open publication No. 10-503841, U.S. Pat. No. 5,807,522). This method involves dispensing a known volume of a reagent at each selected array position, by tapping a capillary dispenser on the support under conditions effective to draw a defined volume of liquid onto the support. This method comprises; filling an aqueous solution of a selected analyte-specific reagent into a reagent-dispensing device having an elongate capillary channel adapted to hold a quantity of the reagent solution and having a tip region at which the solution in the channel forms a meniscus, tapping the tip of the dispensing device against a solid support at a defined position on the surface with an impulse effective to break the meniscus in the capillary channel and deposit a selected volume between 0.002 and 2 µl of solution onto the surface, and repeating the above steps until the microarray is formed.

Further, a method of performing array-based hybridization assays using thermal inkjet deposition of sample fluids is disclosed (U.S. Pat. No. 6,221,653, Japanese laid-open publication No. 11-187900). Furthermore, there is a method using pins and rings or slotted tip pins.

While such methods allow generation of arrays, they are hampered by a severe limitation.

In order to be re-usable, they must be washed between applications of different reagents. The washing step needed when sets of reagents are changed is a slow process that reduces throughput when generating arrays. In addition, if the washing step is not complete, there is possibility of cross-contamination, on the occasion of reusing the same tips.

Further, when the various proteins are treated as reagents, even if a washing step is included, there is a problem that proteins cannot be completely removed and re-using cannot be executed.

Furthermore, there is another problem in that the pins and jet components cannot be autoclaved during the manufacture of the arrays.

Consequently, the present invention aims to resolve the problems outlined above. A first object is to provide a samples delivering device, a method of manufacturing a samples applicator, a method of delivering samples, and a base activation device that allows manipulation of large numbers of different samples, efficiently and promptly.

A second object is to provide a samples delivering device, a method of manufacturing a samples applicator, a method of applying samples, and a base activation device that can be easily produced, the cost of production is reduced and the sample applicator is disposable, does not require washing, and has no contamination or carry-over concerns.

A third object is to provide a samples delivering device, a method of manufacturing a samples applicator, a method of delivering samples, and a base activation device that can be made in a sterile form for microbiological application.

A forth object is to provide a samples delivering device, a method of manufacturing a samples applicator, a method of delivering samples, and a base activation device that can efficiently and promptly manufacture arrays where a large number of samples are arranged.

A fifth object is to provide a samples delivering device, a method of manufacturing a samples applicator, a method of delivering samples, and a base activation device that have such a versatility that samples can be delivered without being restricted by shape, size, or type of the base.

SUMMARY OF THE INVENTION

In order to resolve the above problems, a first aspect of the invention is a samples delivering device comprising; one or more sets of vessels capable of accommodating fluids containing predetermined samples to be delivered to a base or vessels, a samples supply section having a samples applicator wherein two or more retention tips capable of retaining a small quantity of fluids by being dipped in each of said fluids accommodated in the vessels are arranged according to an arrangement of said vessels, and a transfer means for relatively moving between said base and said one or more sets of vessels, and said applicator.

In this description, "predetermined samples" include, for example, organic materials of low molecular weight or high molecular weight such as nucleic acid, protein, and sugar. "Fluid" includes not only a liquid, but also a semiliquid with viscosity.

"Retention tip" is a tip with a function whereby small quantities of fluids can be retained. The shape of the retention tip is determined according to the shape or characteristics of the objective base. For example, in the case where the base is a long and slender thread shape or string shape, preferably, the retention tip has a hook-like shape such as an approximate J-shape, a V-shape or a "<" mark shape. Here, a hook-like shape means a shape opened transversely or upwardly and whereby the retention tips can be relatively moved in the longitudinal direction of the base in contact with the fluids.

Due to the hook-like shape of the retention tip, the contact of the base with the fluids or spotting of the base by the fluids can be performed by upwardly or transversely moving the retention tips relative to the base. Further, relative movement of the base in contact with the fluids, particularly running along the base can be freely performed.

Further, since the retention tip opens upwardly or transversely, the retention capability of the retention tip is high. Therefore, by using a comparatively abundant amount of retained fluids and bringing the fluids in contact with the perimeter of the long and slender base, the perimeter of the curved surface of the base determined in countless directions, can be applied in three dimensions, which is different from the case where applying is performed along a line of the base including only a single direction.

On the other hand, in the case where the base has a shape of a flat plane, for example, the retention tip is preferable one of an approximate L-shape having a pore or a slit.

"A set of vessels" is for example, a microplate having two or more wells. Preferably, the number of the wells is, for example, 48, 96, 384, or 1536, etc.

Preferably, these wells are arranged in matrix-like form, such as six rows×8 columns, 8 rows×12 columns, 16 rows×24 columns, or 32 rows×48 columns.

"Small quantity" means to be for example, the order of about 1 μl. The quantity capable of being retained by the retention tip, namely the quantity of a solution to be applied to the base, is determined by the shape and size of the retention tips. For example, in the case of the hook-like retention tip which is used for the long and slender base, the quantity is determined on the basis of the width along the base and the height or depth of the retention tip. It is preferable that the height or depth of the retention tip is more than the diameter of the base. In the case of the retention tip having a hole or slit, the quantity is determined on the basis of the thickness of the sheet-like member constructing the retention tip and the area of the hole or slit.

"Delivering samples" is performed not only to the base, but also to the vessels, in such a way that the base or the vessel or the liquid accommodated in the vessel comes in contact with the fluids retained in the retention tips of the applicator. Applying corresponds to contacting with the retention tips in a static or dynamic state thereof. Furthermore, time of contacting with the fluid is either momentary or finite. The fixed quantity and fixed area of the samples can be adjusted by the distance moved along the base or each vessel, or the time of contacting with the fluid. Applying in a static state corresponds to spotting which the samples attached in the shape of a spot.

In order to prevent a fluid from adhering to the area contiguous to the retention tip other than the above-mentioned retention tip, it is preferable to cover the surface with a macromolecule coating, especially Teflon, or silicon, to add a hydrophobic character.

As for the samples applicator where the retention tips are mounted, it is preferable to make the samples applicator by processing a thin board or a sheet-like material. As such a material, for example plastics, such as Polycarbonate (transparent thermoplastic material), Polyvinyl acetate, polyethylene, polypropylene, polysulfone, polyvinylidene difluoride, Teflon, metals, or cellulosics that are available in flat thin sheet form. Thin sheet refers to materials of the order of between 1 and 100 μm thick, preferable of the order of between 10 and 100 μm thick and typically about 12 μm thick. Thin sheet materials are preferred because such materials are low cost and can be used to mass produce the disposable samples applicator by a stamping or cutting and folding process at low cost to provide a disposable device.

"Base" is one of the objects to which the above-mentioned samples are delivered, such as a plate-like chip, a long and slender object like a string or thread, or a set of vessels like a microplate. In order to dispose the samples contained in the applied fluid, this base itself needs to have a nature that can be retain the samples. This nature is for example, a permeable nature such as with porosity, irregularities, or foam, or liquid holding nature such as with vessels. Moreover, this base needs to be disposed so as to enable application according to the arrangement of the above-mentioned retention tips. It is possible to conduct various kinds of inspection in a state where the above-mentioned samples and their delivered positions are matched. It is preferable that a biologically activated molecules are fixed to the porous layer etc. of the base. The base is made of a fibrous material such as a monofilament line which does not have a twist, as used in the sporting field for fishing, of a thin diameter of a nylon sewing thread, for example.

With the first aspect of the invention, by merely dipping a retention tip in a well of a container accommodating fluid containing a sample to be delivered, the fluid can be retained on the retention tip, and the fluid containing the sample can be delivered to the base by contacting the base with the fluid in the retention tip. Therefore, an array being an efficient arrangement of many samples, such as a DNA chip, can be manufactured in large quantities with a simple structure and control, at low cost.

Further, cross-contamination can be surely avoided, and reliable processing can be performed. Moreover, by using a suitable retention tip having a shape or size corresponding to the shape or size of the base, diverse and versatile processing can be performed.

A second aspect of the invention is a samples delivering device, wherein the samples applicator is dismountably fitted to the sample supply section.

With the second aspect of the invention, since the applicator is dismountably fitted and the used ones can be sequentially replaced with a new one, many samples can be delivered, while preventing cross-contamination. In addition, since the applicator can be manufactured at low cost, processing cost can be reduced.

A third aspect of the invention is a samples delivering device, further comprising, in the case that the base is shaped so as to be a long and slender thread shape or string shape; a base feeder for arranging and tensioning the base along a path determined according to the arrangement of the retention tips in a manner that the base can run along the path and come in contact with the fluid retained in the retention tips, and a transfer means comprising a running driver for running the base along the path, and an applicator transferring device for transferring the retention ends relative to the base.

In this description, "a base feeder" is, for example, an apparatus where the long and slender base is arranged along a predetermined path from a supply reel or a roller upstream to a take-up reel or a roller downstream. Between the reel or roller upstream and the one downstream, other rollers can be arranged at intervals along the path.

Furthermore, in order to tension the running base, for example, a turning force should be added to the reel or roller upstream so as to advance the base in the running direction, and a little stronger turning force should be added to the reel or roller downstream.

In order to apply fluid to the long and slender base, it is preferable that the base comes in contact with the fluid retained in the retention tip in a manner that the perimeter of the base is steeped in the fluid. Hence, the shape of the retention tip is preferably open so as to be hook-like. The liquid amount is determined according to the diameter of the base.

With the third aspect of the invention, the long and slender base is arranged in a manner that the base can run under tension along the path determined according to the arrangement of the applicator. Therefore, the samples can be easily and efficiently delivered by combining the running of the base with the transfer of the applicator.

A fourth aspect of the invention is a samples delivering device, wherein the applicator is a comb-like applicator, with the retention tips arranged at predetermined intervals so as to be comb-like.

In this description, "predetermined intervals" is determined in consideration of the interval of neighboring vessels belonging to a set of vessels, for example the interval of the wells of a microplate or the interval between adjacent samples on the base.

With the fourth aspect of the invention, since a plurality of retention tips can simultaneously contact with the base, the samples can be efficiently and promptly delivered.

A fifth aspect of the invention is a samples delivering device, wherein the applicator is a matrix-like applicator, with the retention tips arranged at predetermined intervals so as to be matrix-like, the base feeder tensions and arranges the base in a manner that the base threads its way through rows or columns of the matrix and can run in the row direction or column direction of the matrix. For example, the matrix-like applicator is assembled by placing the comb-like applicator in plural columns, or by putting other matrix-like applicators together, or by arranging each applying component so as to be matrix-like.

With the fifth aspect of the invention, since a plurality of retention tips can be simultaneously contacted with the base, the samples can be efficiently and promptly delivered.

A sixth aspect of the invention is a samples delivering device, wherein the applicator comprises two or more applying components made of thin board or a sheet-like member, wherein each applying component comprises an arm section shaped so as to be vertically long or tapered downwardly, and the retention tip shaped in a manner that the sheet-like member is bent so as to be opened upwardly or transversely relatively to the arm section.

With the sixth aspect of the invention, the applicator can be easily manufactured from sheet or thin plate. Therefore, the production cost of the applicator can be reduced, and a disposable applicator can be provided.

A seventh aspect of the invention is a samples delivering device, wherein the samples applicator comprises two or more applying components made of thin board or a sheet-like member, and each applying component comprises an arm section shaped so as to be vertically long or tapered downwardly, and the retention tip has a hole or a slit. The portion of the retention tips having a hole or a slit, may be bent in the axial direction of the arm section.

With the seventh aspect of the invention, the applicator can be easily manufactured from sheet or thin plate. Therefore, the production cost of the applicator can be reduced, and a disposable applicator can be provided.

An eighth aspect of the invention is a samples delivering device, wherein the samples applicator comprises two or more applying components, and each applying component comprises a lid part capable of being fitted to an opening of the vessel in a manner that can close up the vessel, and a retention tip mounted under the lid part so that the retention tip is confined within the vessel when the vessel is closed up by the lid part.

With the eighth aspect of the invention, instead of accommodating a prepared sample in a vessel beforehand, the sample can be efficiently prepared in this vessel. Therefore, an increase in efficiency, speeding up, or continuity of the whole process can be achieved. Further, evaporation of the liquid can be avoided by sealing the vessel with the lid part.

A ninth aspect of the invention is a samples delivering device, wherein the feeder comprises gear-like rollers have a plurality of sharp cogs in a manner that each cog comes in contact with the base at positions between delivered samples in an interval equal to or an integer interval of the delivered samples on the base, and the base is routed and arranged through the rollers.

With the ninth aspect of the invention, the gear-like rollers having a plurality of sharp cogs are mounted in the feeder and each cog comes in contact with the base at positions between delivered samples in the same interval as that of the delivered samples mounted on the base. Therefore, since the rollers do not come in contact with the delivery positions, directly, cross-contamination can be prevented.

A tenth aspect of the invention is a method for manufacturing a samples applicator comprising steps of bending an edge of a rectangular thin board or sheet-like member in a manner that an opening defined by the bent edge and a surface thereof faces in a direction of the surface or in a direction perpendicular to the surface, and cutting the bent thin board or sheet-like member so that several retention tips and arm sections are obtained.

With the tenth aspect of the invention, the applicator can be easily manufactured from sheet or thin plate. Therefore, the production cost of the applicator can be reduced, and a disposable applicator can be provided.

An eleventh aspect of the invention is a method, wherein at the cutting step, the bent thin board or sheet-like member is cut in a manner that retention tips are completely separated from one another or are arranged at predetermined intervals so as to be comb-like.

In this description, "predetermined intervals" is determined in consideration of the interval between the delivery positions on the base, and the interval between the neighboring wells of the microplate.

With the eleventh aspect of the invention, the applicator can be easily manufactured from sheet or thin plate. Therefore, the production cost of the applicator can be reduced, and a disposable applicator can be provided.

A twelfth aspect of the invention is a method of delivering samples, comprising the steps of retaining a small quantity of fluid in two or more retention tips of a samples applicator arranged according to the arrangement of vessels, by relatively transferring the samples applicator to one or more sets of vessels accommodating fluids containing predetermined samples to be delivered to a base or vessels, and dipping the retention tips into the fluids, and delivering the fluid retained in the retention tips to the base or one or more sets of vessels by relatively moving between the retention tips and the base or the vessels.

With the twelfth aspect of the invention, by merely dipping a retention tip in a well of a container accommodating fluid containing the sample to be delivered, the fluid can be retained on the retention tip, and the fluid containing a sample on a base can be delivered by contacting the base with the fluid in the retention tip. Therefore, the array being an efficient arrangement of many samples, such as a DNA chip, can be manufactured in large quantities by a simple structure and control, at low cost.

A thirteenth aspect of the invention is the method, further comprising a step of rejuvenating the samples applicator by replacing the used samples applicator with a new one.

With the thirteenth aspect of the invention, since the applicator is dismountably fitted and the used ones can be replaced sequentially with new ones, many samples can be delivered, while preventing cross-contamination. In addition, since the applicator can be manufactured at low cost, processing cost can be reduced.

A fourteenth aspect of the invention is the method, wherein the step of applying comprises, in the case where the base is shaped so as to be a long and slender thread shape or string shape, a step for running the base tensioned along a path determined according to the arrangement of the retention tips, in a manner that the base can come in contact with the fluids retained in the retention tips.

With the fourteenth aspect of the invention, the long and slender base is arranged in a manner that the base can be run under tension along the path determined according to the arrangement of the applicator. Therefore, the samples can be easily and efficiently delivered by combining the running of the base with the transfer of the applicator.

A fifteenth aspect of the invention is the method, where in the running step, the base runs along a path disposed in the direction of arrangement of the retention tips of the comb-like samples applicator.

With the fifteenth aspect of the invention, since a plurality of retention tips can simultaneously contact with the base, the samples can be efficiently and promptly delivered.

A sixteenth aspect of the invention is the method, where in the running step, the base runs along a path disposed in the direction of rows or columns of a matrix corresponding to the arrangements of the retention tips of the matrix-like samples applicator, in a manner that the base threads its way through the rows or columns of the matrix.

With the sixteenth aspect of the invention, since a plurality of retention tips can simultaneously contact with the base, the samples can be efficiently and promptly delivered.

A seventeenth aspect of the invention is a method comprising; a step of mixing, diluting or altering the fluids in the retention tips by relatively transferring the retention tips to an other one or more sets of vessels and dipping the retention tips into fluids of the vessels after the step of retaining.

With the seventeenth aspect of the invention, before application by the retention tip, the fluids retained in the retention tips can be mixed with the other liquid, diluted, or altered. Therefore, in activation chemistry, such an advantage of adding the reagent to the base "at the last moment", can be obtained before fixing. Particularly, in the case when the contents of cells or bacteria are to be fixed to the base, they can be dissolved immediately before application to the base.

An eighteenth aspect of the invention is a base activation device comprising a tube capable of being threaded by a thread shaped or string shaped long and slender base, a feeder for disposing and tensioning the base along a path determined by a shape of the tube in a manner that the base can run along the path, and a running driver for driving to run the base through the tube, wherein the tube is shaped so that both ends of the tube are curved upwardly so that a solution for activation can be accommodated within the tube.

With the eighteenth aspect of the invention, the tube is formed so as to be a sort of container accommodating the solution for activation. Therefore, the base can come in contact with the solution while passing through the tube. Consequently, by using the device, the base can be activated, and can be immersed in the solution for a long time. Further, by using the feeder, the base can be tensioned and run in a manner to prevent tangling. Consequently, the base can be reliably activated by a simple mechanism.

DESCRIPTION OF THE PREFERRED EMBODIMENTS

A samples delivering device, a method of manufacturing a samples applicator, and a method of delivering samples, of the embodiments of the invention are explained based on the drawings. These embodiments should not be interpreted as limiting the invention unless particularly specified.

Figure 1:
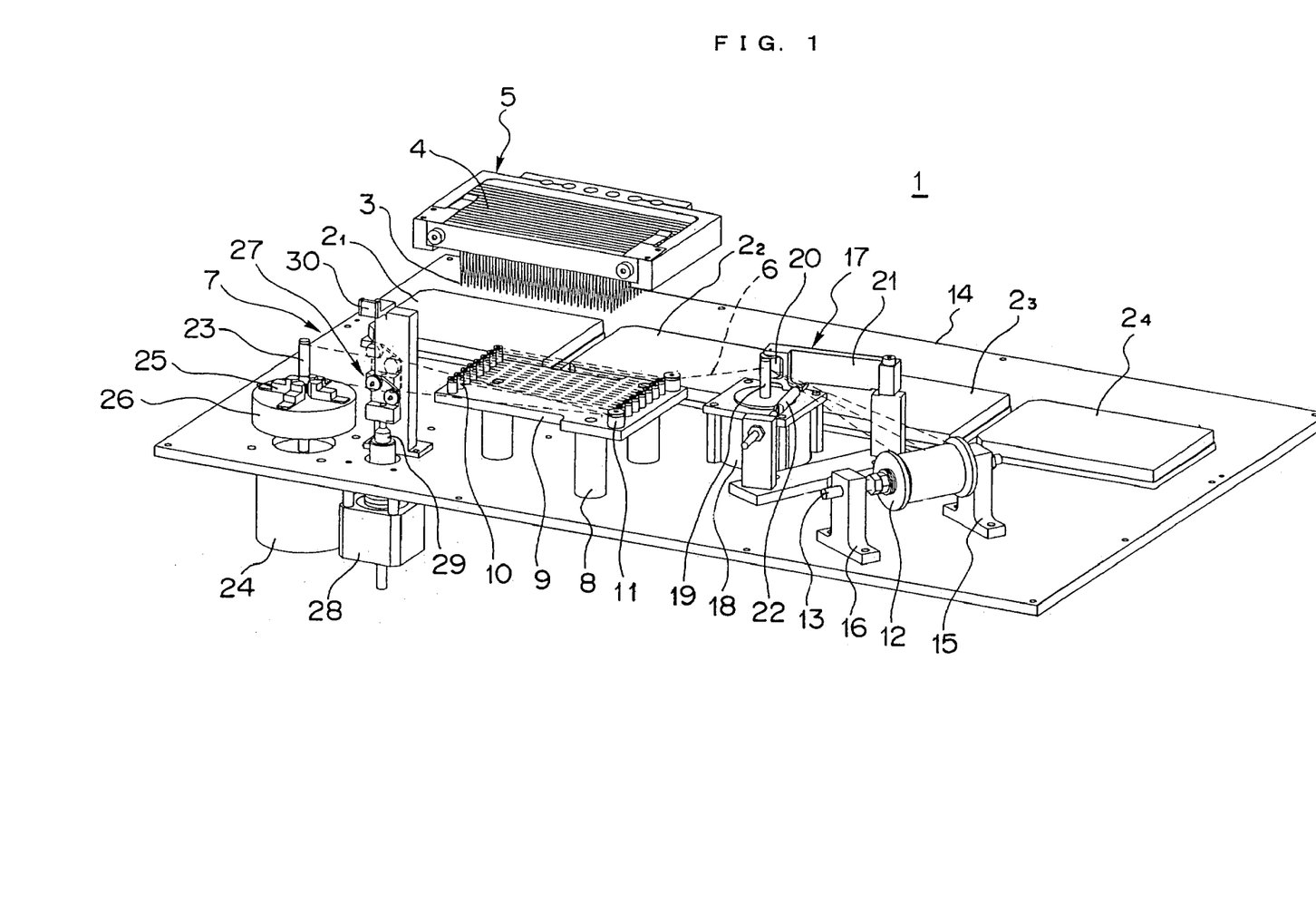
FIG. 1 is a perspective view generally showing a samples delivering device of a first embodiment of the invention.

FIG. 1 shows an approximate overview of a samples delivering device 1 of a first embodiment.

The samples delivering device 1 is used so that multiple samples can be simultaneously treated. The samples delivering device 1 comprises a plurality of (four in this example) microplates $2_1$, $2_2$, $2_3$, $2_4$ having a plurality of wells accommodating various liquids including a plurality of extracted DNA of samples which are arranged so as to be matrix-like (24×16), and a samples supply section 5 having a matrix-like applicator 4 with two or more hooks 3 corresponding to the retention tips capable of retaining a small quantity of fluid by being dipped in each of the fluids accommodated in the wells of the microplates $2_1$, $2_2$, $2_3$, $2_4$, are arranged according to the arrangement of the wells.

Furthermore, the samples delivering device 1 comprises a base feeder 7 for arranging and tensioning a string-like base 6 to which predetermined samples are delivered, along a path determined according to the arrangement of the hooks 3 in a manner that the string-like base 6 can run along the path and come in contact with the fluid retained in the retention tips.

The above-mentioned string-like base 6 is a string with a porous surface layer, and the biologically activated molecule is fixed to the porous layer of the string. This material component provides the porous surface layer with mechanical hardness. As the string-like base 6, a line of a nylon sewing thread is used, for example.

The base feeder 7 comprises a base table 9 supported by pillars 8, and fifteen small diameter rollers 10 and two large diameter rollers 11 rotatably supported by the base table 9. The string-like base 6 is routed and arranged through these seventeen rollers 10, 11 so that the base 6 threads its way through rows of the matrix (or columns of the matrix) and can run in the row direction or column direction of the matrix, and so that the base 6 can come in contact with all the hooks 3 of the matrix-like samples applicator 4.

Therefore, the diameter of the small diameter roller 10 is determined according to the interval of neighboring wells of the microplates $2_1$, $2_2$, $2_3$, $2_4$ or hooks. Each roller 10, 11 is a gear-like roller which has a plurality of sharp cogs around the circumference of the roller. Edges of the cogs are formed so as to come in contact with the base 6 at positions between fixed samples in an interval equal to or an integer interval of the delivered samples on the base. It is preferable that the base is routed and arranged through rollers so that the cogs come in contact with the positions between the positions fixed by the samples.

On the upstream side of the base table 9, there are a supply reel 12 for supplying the string-like base 6, a horizontal axis 13 of the supply reel 12 parallel with a plate 14, and a fixed supporter 15 and a movable supporter 16 for supporting the supply reel 12. The tension can be easily adjusted by using the movable supporter. A feed roller assembly 17 is provided between the supply reel 12 and the large diameter roller 11. The feed roller assembly 17 comprises a feed motor 18, a rotary shaft 19 driven by the feed motor 18, a roller 20 pressed on the rotary shaft 19, an arm 21 for rotatably supporting the roller 20 and being itself rotatably supported, and a rod-like member 22 for adjusting the tension of the base 6 running in a manner sandwiched between the roller 20 and the rotary shaft 19 by adjusting the pressure between the roller 20 and the rotary axis 19.

On the downstream side of the base table 9, there are a take-up reel 23 for taking up the string-like base 6, a core winding motor 24 for rotating the take-up reel 23, a jaw 25 self centering chuck 26, and a wrap guide assembly 27. The wrap guide assembly 27 comprises a wrap guide linear motor 28, an actuator 29 driven to move vertically by the motor 28, and a cutter 30 for cutting the string-like base 6.

Further, the samples delivering device 1 comprises an applicator transferring means, which is not shown in the drawings, for vertically and horizontally transferring the applicator 4 relative to the base table 9 where the string-like base 6 is arranged. The feed motor 18 and the wrap guide linear motor 24 corresponds to the running driver, and the applicator transferring means and the running driver corresponds to the transfer means. The applicator transferring means is preferably a robot arm for holding and transferring the applicator 4.

Figure 2:
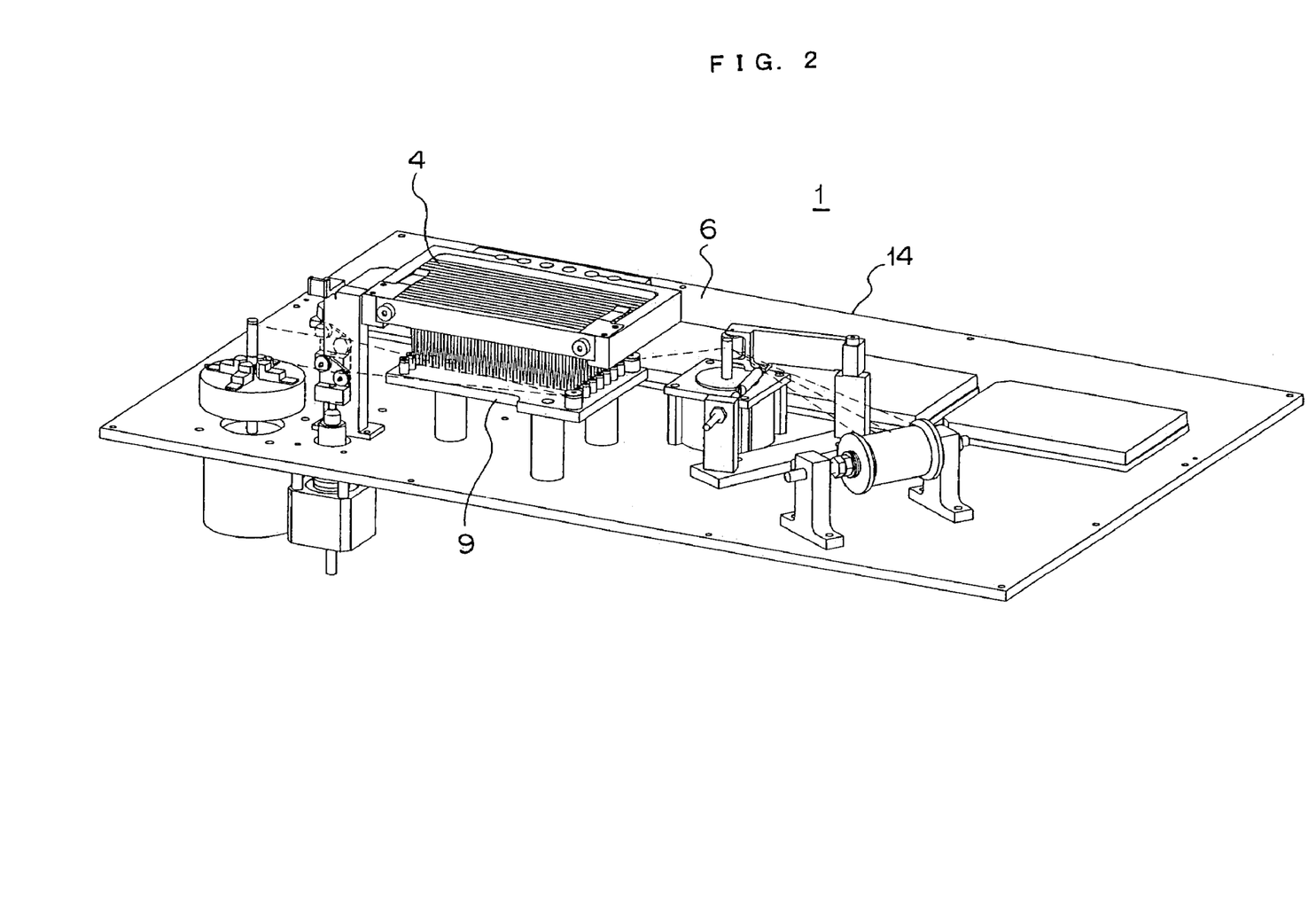
FIG. 2 is a perspective view generally showing the samples delivering device of the first embodiment of the invention.

FIG. 2 shows that the applicator 4 is transferred downwardly and the string-like base 6 is disposed in contact with the fluids in the hooks 3.

Figure 3:
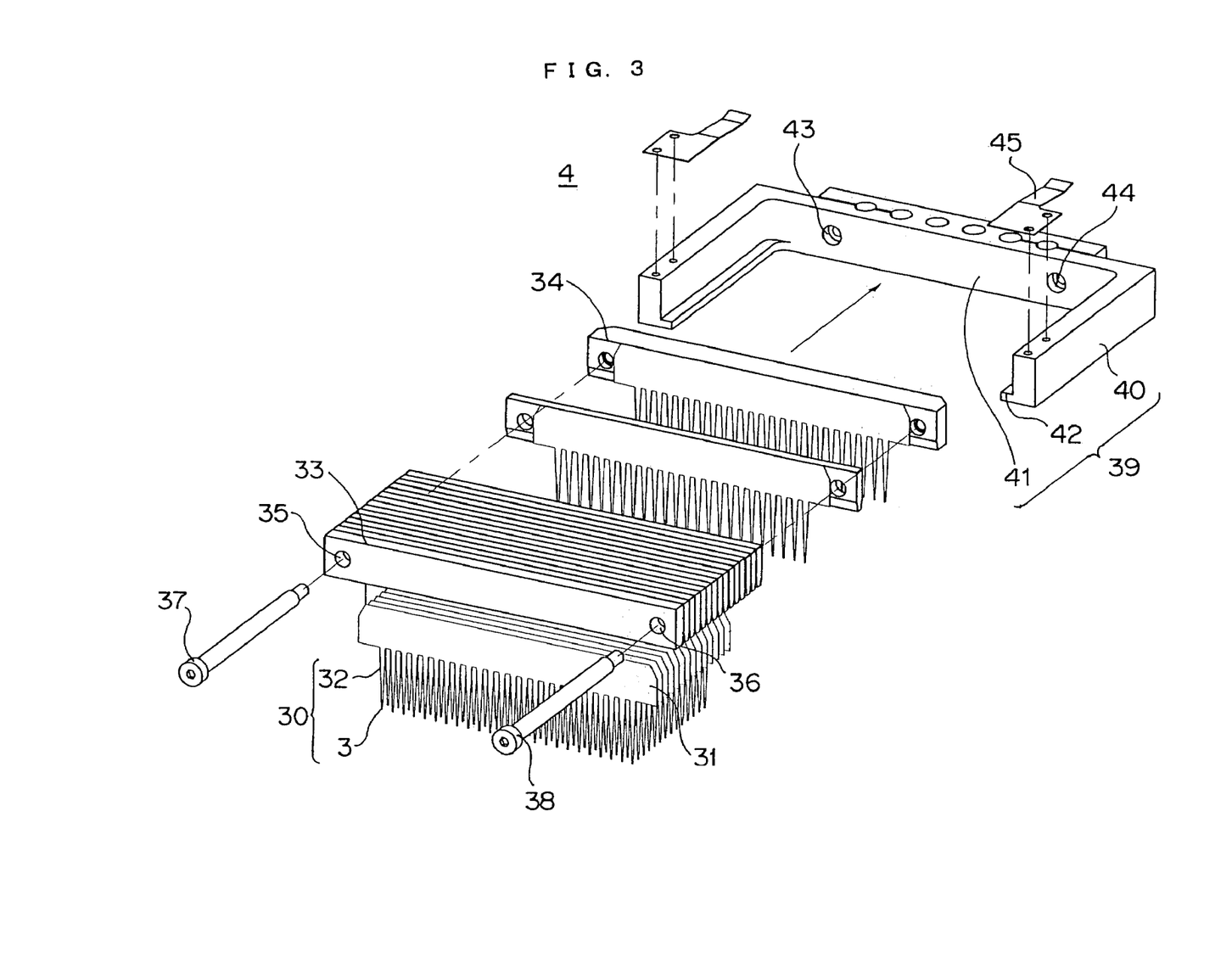
FIG. 3 is a perspective view showing an applicator of the first embodiment of the invention.

FIG. 3 shows the matrix-like samples applicator 4 in detail.

The matrix-like samples applicator 4 is generally made from a sheet-like member. The matrix-like samples applicator 4 has twenty four comb-like applicators 31 having many applying components 30. Sixteen applying components 30 comprising a hook 3 and an arm section 32 are arranged so as to be comb-like, in this example. Generally, the applying components 30 are arranged in matrix form so as to be sixteen rows×twenty-four columns. As the sheet-like member, for example, it is preferable that it is made of transparent plastics etc.

The applying components 30 comprises the arm section 32 formed so as to be tapered downwardly, and the hook 3 which is mounted below the arm section 32 and is made by bending the sheet-like member in a manner to be opened upwardly.

The comb-like applicator 31 is attached to a gripper-spacer plate 33 on the upper part of the arm section 32 by an adhesive. The shape or length etc. of the arm section 32 is chosen to be consistent with:

(1) ergonomics of the robotic equipment, (2) the base or vessels receiving the samples, and (3) the vessels holding the materials to be dispensed.

The hook 3 is designed to perform the specific dispensing function and to hold a specific volume of liquid to be dispensed. As a preferred example, materials for the applying component 30 are made of thin plate-like members made of plastics such as polycarbonate, whose depth is about 200 μm. The arm section 32 is formed so as to be tapered downwardly or of an inverted triangle shape and is formed integral with the hook 3. The hook 3 is bent so as to form a substantial V-shape opened upwards. Hence, the applying element 30 is formed overall so as to be substantially J-shaped from the sideways view.

Each comb-like applicator 31 is attached to twenty-four thin plate-like gripper-spacers 33, 34 by using an adhesive or double sided adhesive tape. The gripper-spacers 33, 34 have two through holes near both ends thereof respectively. Two shoulder bolts 37, 38 are mounted so that they penetrate the through holes 35, 36 respectively. The adhesive is preferably one that can be easily removed after being attached, so that the comb-like applicators 31 are dismountably fitted to the gripper-spacers 33, 34.

Further, an adapter 39 is mounted so as to bunch together these gripper-spacers 33 and 34 and to enable moving of the applicator 4 by connecting to the applicator transferring device, which is not shown in the drawings. The adapter 39 comprises two side parts 40 formed so as to be substantially U-shaped, and a central part 41. With the side parts 40, an edge part 42 is mounted at the bottom thereof in a manner so as to slightly project inwardly, for mounting the gripper-spacers 33 and 34 thereon. With the central part 41, there are tapped holes 43, 44 to fix the gripper-spacers 33 and 34 by threading with the shoulder bolts 37 and 38. Reference numeral 45 denotes a holder for preventing rising of the comb-like applicator 31.

Figure 4:
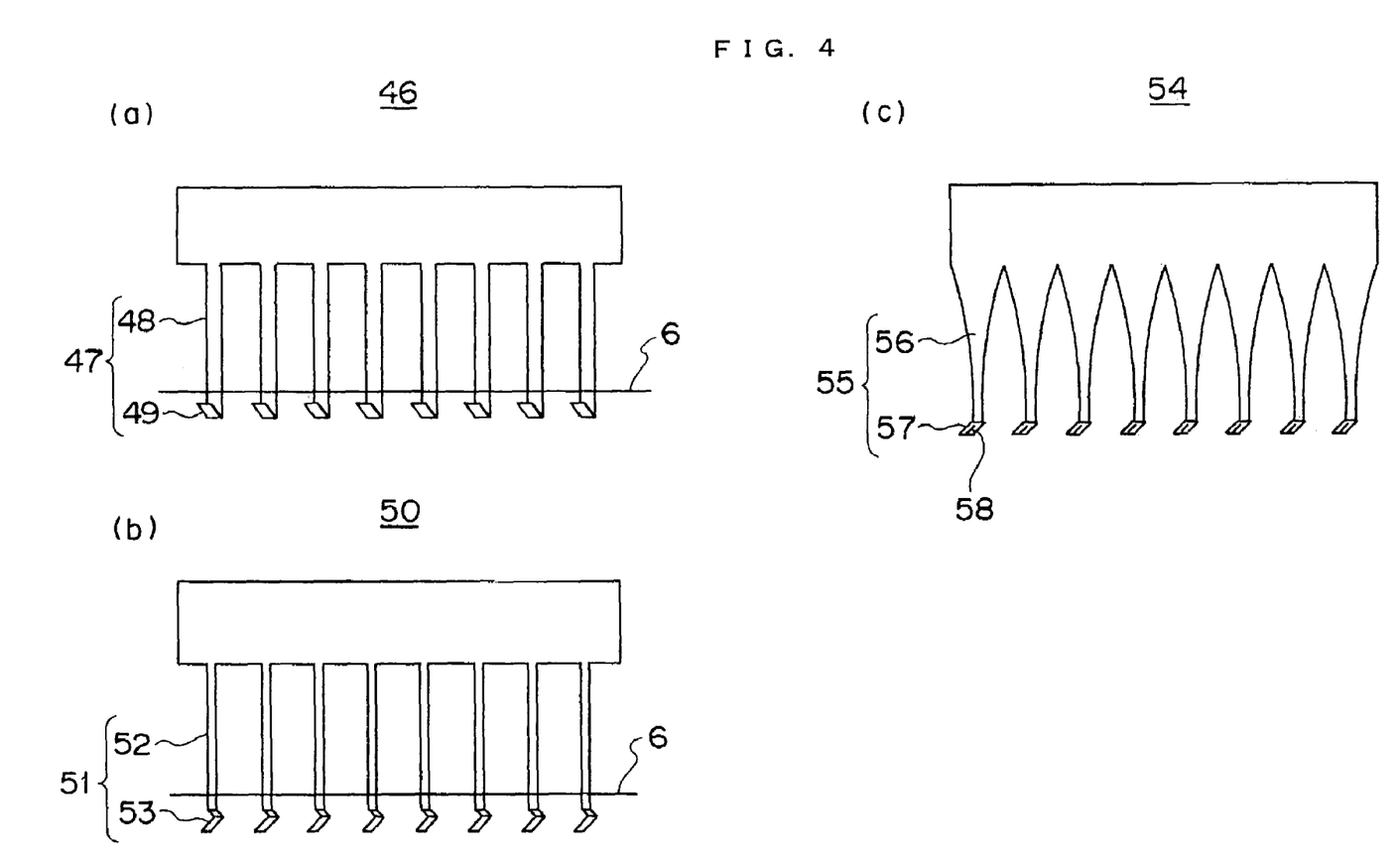
FIG. 4 is a view showing an example of a comb-like applicator of the first embodiment of the invention.

FIG. 4(a) shows a comb-like applicator 46 of another example. The comb-like applicator 46 has eight applying components 47. Each applying component 47 comprises a long, instead of being an inverted triangle, arm section 48, and a hook 49 mounted under the arm section 48, which is formed so as to be substantially V-shaped.

FIG. 4(b) shows a comb-like applicator 50 of yet another example. The comb-like applicator 50 comprises eight applying components 51. Each applying component 51 comprises a long arm section 52, and a substantially ">" mark shaped hook 53 mounted under the arm section 52 as the retention tip.

FIG. 4(c) shows a comb-like applicator 54 of yet another example. The applicator 54 is used for arranging samples on a planar base which is not shown in the drawings, instead of the string-like base 6. Each comb-like applicator 54 has eight applying components 55. The applying component 55 comprises an arm section 56 formed so as to be tapered downwardly and a retention tip 57 mounted under the arm section 56, being bent so as to be substantially L-shaped. The retention tip 57 has a slit 58.

The manufacturing process of the comb-like applicators 46 and 50 shown in FIGS. 4(*a*) and 4(*b*) will now be explained.

A rectangular sheet with a thickness of about 200 microns made of polycarbonate having a depth of about 200 microns is cut from a roll. The sheet of rectangular shape with a thickness of about 200 microns made of polycarbonate is roll stock. This sheet is bent along a straight line parallel to one edge of the sheet, near to the edge. A metal ruler is suitable for performing such straight bending. Moreover, a tool for bending sheet, called a "box brake", is useful.

A tight hook can be formed by pressing down the ruler on the folded plastics. According to this way, all applying components can be made at the same time and achieve alignment by having simultaneous folding. The hard part is holding the ruler down on the sheet while bending. "C" clamps help, but a box brake is better if the hooks are not small.

Next, the "J" shaped applying component which consists of the arm section and the hook is made by cutting the above-mentioned thin plate. On this occasion, it is preferable to lay the sheet so the curved piece is pointing down, and to use a sharp razor blade and a metal ruler to guide the cut, and to start away from the hook end. It is difficult to cut in one stroke, being better to cut several times with the razor blade until the hook is free from plastic sheet. In the case of having such curves as shown in FIG. 4(*c*), cutting by a die is easier.

In making the ">" shaped hook in FIG. 4(*b*), the metal ruler is placed over the "J" shaped hook and the handle is lifted back. It is also possible to "stamp" the hooks out of plastic sheet material with a die. It is also possible to cut different shapes with a laser cutter, instead of using a die. A "V" shape grove in a metal plate and a metal stamp may be used to make the ">" shape hook. In order to align the applying components, for example, the ruler is laid over all the hooks, and aligned with the tops of the applying components, and bend backward to get a good alignment and uniform shape for all the hooks.

Figure 5:
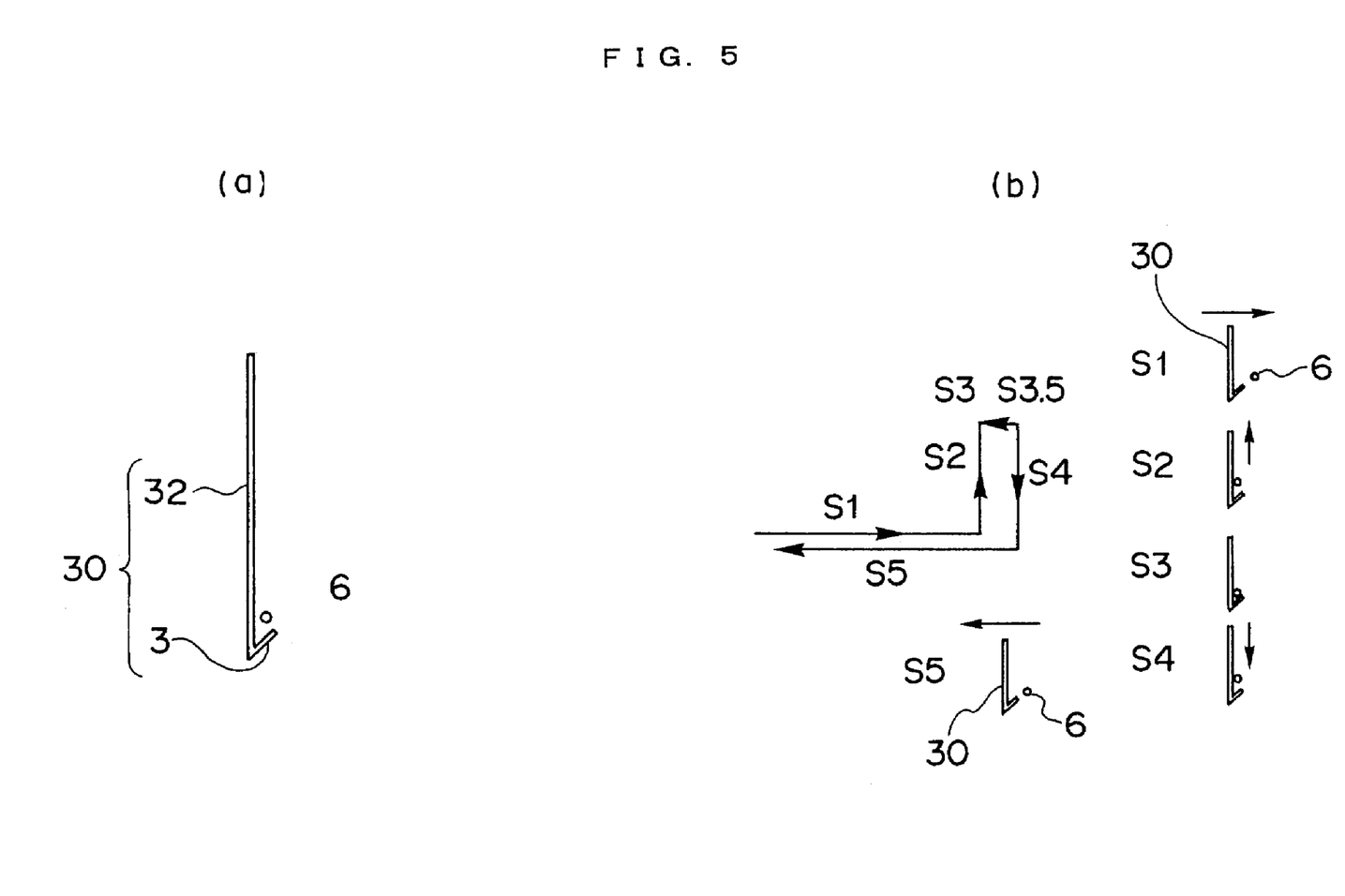
FIG. 5 is a view showing movement of the applicator of the first embodiment of the invention.

Based on FIG. 5(*a*), an explanation is given of the movement of delivering the samples to the thread shaped or string shaped base 6 by using the substantially "J" shaped hook 3 of the applying component 30 of the samples delivering device 1 of the embodiment.

The most interesting thing about the hooks 3 made of plastics is that they can pick up a suitable amount of liquid, about 1 micro liter by dipping into suspensions including samples accommodated in the wells of the microplate 2. For this, sufficient liquid is required so that the hooks can be submerged by dipping. The hook can pick up a 0.5 micro liter droplet from a Petri dish or piece of Parafilm if the dish or film is pressed against the side of the hook 3.

By using the applicator transferring device which is not shown in the drawings, the hooks 3 are transferred to the microplate 21, are dipped in the liquid accommodated in the wells, and retain the liquid. As shown in FIG. 2, the matrix-like samples applicator 4 retaining liquids in each hook 3 thereof is lowered until each applying component 30 approaches near the string-like base 6 configured at the base table 9, by using the applicator transferring device which is not shown in the drawings. The hooks 3 can also be transferred to other microplates which are not shown, according to process requirements.

Next, as shown in FIG. 5(*b*), at Step S1, the hook 3 is horizontally transferred and approaches the string-like base 6, so that the base 6 may be simultaneously located in positions higher than those of the hooks 3. The string-like base 6 is arranged and tensioned in a manner that it is routed through the rollers 10 and 11 on the base table 9. At step S2, the hook 3 is lifted until it meets with the string-like base 6. Then, at Step S3, the hooks 3 come in contact with the string-like base 6 so that the external surface of the string-like base 6 is immersed in the liquids retained in the hooks 3. This contact state of the hooks 3 is shown in FIG. 5(*a*). In this case, the hook 3 applies to the string-like base 6 with the string-like base 6 in a static state.

Moreover, in a state with the hook 3 of the applying component 30 contacting the base 6, the applying component 30 can be moved a minute distance along the longitudinal direction of the base 6, so as to extend the application area according to use. In addition, the static state may be maintained for a predetermined time, for example 2-3 minutes, according to the kind of samples to be fixed, the reaction, the use, etc.

At Step S3.5, this applying component 30 is moved a minute distance so as to it may separate from the string-like base 6 horizontally. Thereafter, at Step S4, in a state where the applying component 30 is separated from the string-like bases 6, the applying component 30 is lowered. According to the embodiment, in a state where each applying component 30 is separated from the string-like bases 6 to which the application has already been carried out, the applying component 30 is lowered from the base 6. Hence, the possibility of mutual contact can be reduced and cross-contamination can be reliably avoided. At Step S5, the applying components 30 and hence the applicator 4, are moved away from the base 6.

On the other hand, as shown in FIG. 4(*b*), in order to use the applying components 51 having a substantially "<" shaped hook 53, the hooks 53 are transferred to a position where the string-like base 6 is located slightly higher than that of the hooks 53 (similar to the case of "J" shaped hooks).

When the applying component 51 is brought forward toward the string-like base 6, the arm section 52 bends and all the hooks 53 slip into place and come in contact with the string. The hooks keep close to the string, so as not to touch too much. This method requires no precise alignment between the base 6 and the hooks 53. Also, this method allows the comb-like applicator having the hooks 53 to be raised after coming in contact with the string-like base 6. In this case, the thickness of the plastic sheet is important. The more thick the plastic sheet is, the more high the rigidity is, though a plastic sheet of high rigidity is harder to bend. Hence, it is preferable that a thin plastic sheet is used for the lower arm section 52 and the hook 53 and a thicker plastic sheet is used for the upper arm section 52 etc.

In addition, a different operation is necessary when the arrangement of the applicator or the shape of the retention tips is different.

After application at the 24×16=384 locations by transfer of the applicator 4 is completed, the applied length of the string-like base 6 arranged on the base table 9 runs along the path and is wound onto the take-up reel 23 using the winding motor 24 and the feed motor 18, being the running driver. Then the non-applied string-like base 6 is supplied to the base table 9 from the supply reel 12, and the 384 applications are newly performed by the processing mentioned above.

In that case, the applicator 4 is replaced with one having new applying components 30. The applying components 30 are dipped in the liquids in which are suspended samples, accommodated in the next microplate $2_2$, retain the liquid, and the above-mentioned processing is performed. Thereafter, processing will be similarly performed one by one for the microplates $2_3$ and $2_4$.

In addition, in order to apply tension to the base 6, the torque of the winding motor 24 which drives the take-up reel 23 is controlled so as to become larger than the torque of the feed motor 18.

Figure 6:
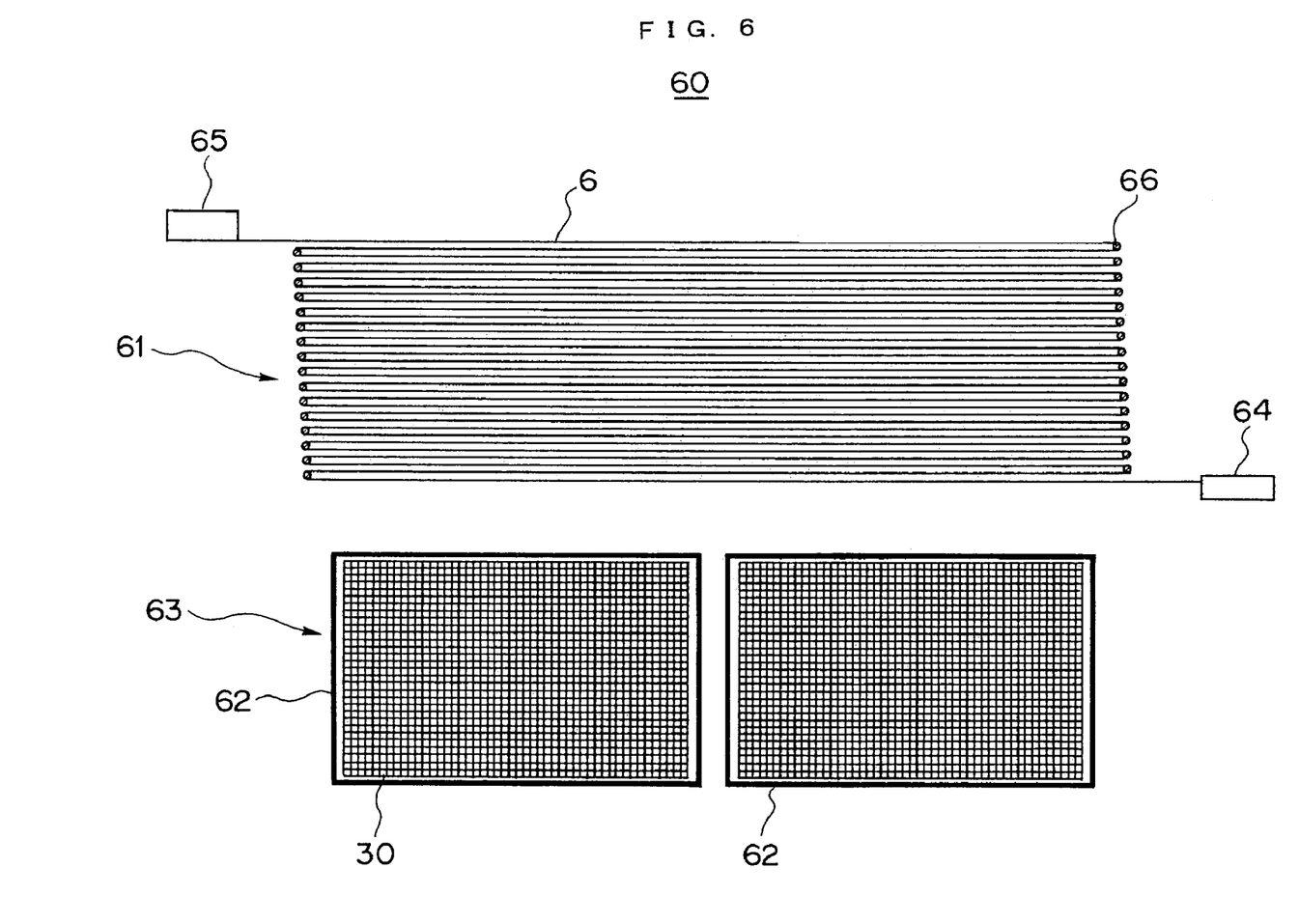
FIG. 6 is a view showing a matrix-like application section and a base feeder according to a second embodiment of the invention.

FIG. 6 shows a samples delivering device 60 of a second embodiment. This samples delivering device 60 comprises a base feeder 61 and a sample supply section 63 having two matrix-like applicators 62 by which the applying components 30 are arranged in the shape of a matrix, 32 rows×48 columns (=1536 pieces), and application can be simultaneously performed at 3072 positions.

As shown in FIG. 6, the base feeder 61 comprises a supply reel 64, a take-up reel 65, thirty-two rollers 66 mounted at fixed intervals in accordance with the path of the base 6 between these reels, and a motor which carries out rotation drive of the supply reel 64 and the take-up reel 65, which is not shown in the drawings.

With this base feeder 61, by using the thirty-two rollers 66, the string-like base 6 is configured so that thirty-two columns may be formed substantially. The string-like base 6 is routed so as to be able to run from the supply reel 64 to the take-up reel 65. The matrix-like samples applicator 62 is transferred by using a motor etc. as a transfer means not shown in the drawings.

The interval between each sequence of the thirty-two columns of the string-like base 6 of the base feeder 61, and consequently the diameter of the rollers 66, is formed so as to be associated with or be equal to the interval between the columns of the matrix-like applicator 62, and the length of each of the columns of the base 6 is associated with or equals the intervals of the forty-eight rows of the applicator 62.

With the samples delivering device of the present embodiment, since a sample can be fixed at 3072 positions at once to the string-like base 6, efficiency is much higher.

Figure 7:
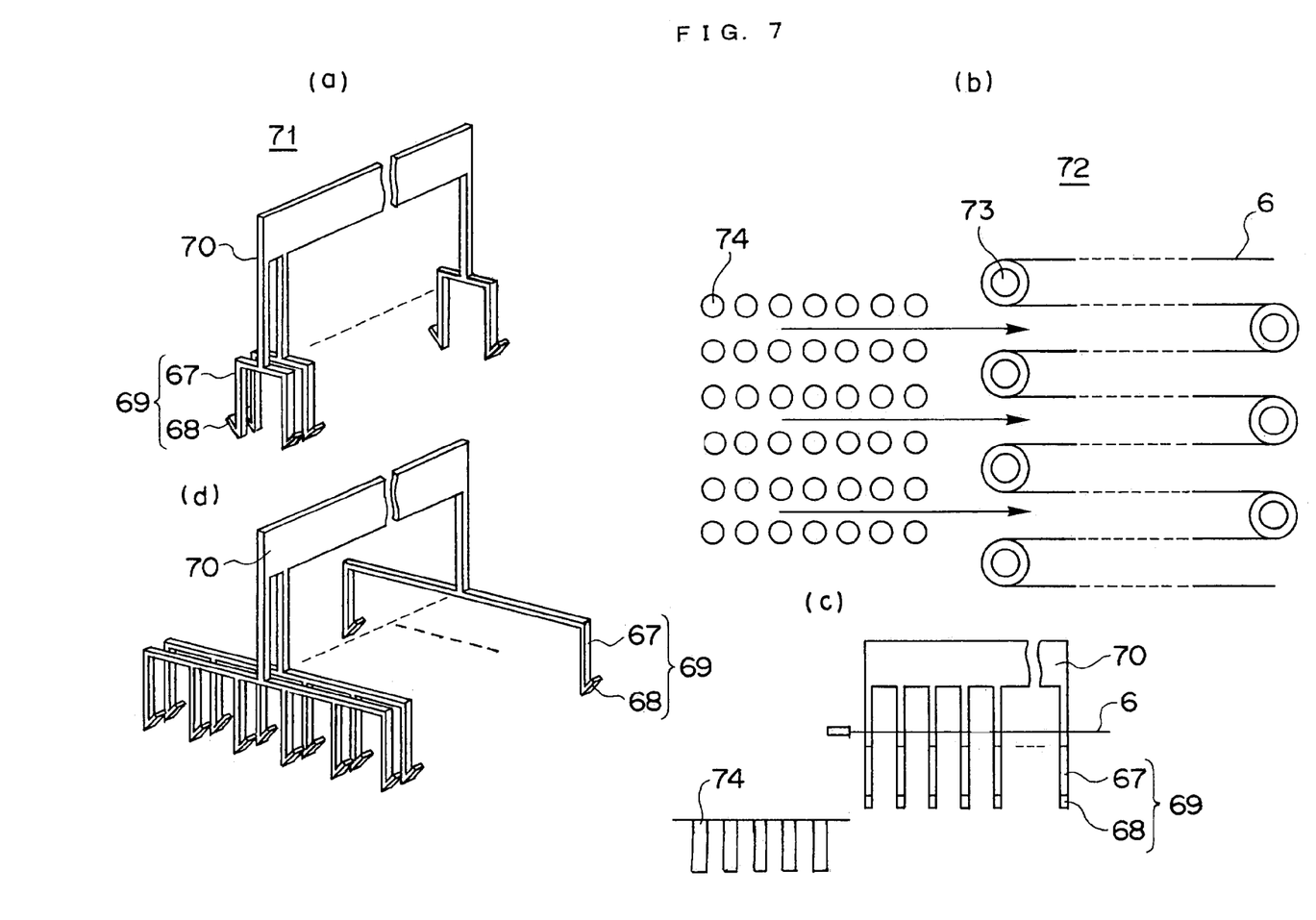
FIG. 7 is a view showing a matrix-like application section according to a third embodiment of the invention.

FIG. 7(a) shows a samples delivering device of a third embodiment. The samples delivering device has a matrix-like applicator 71 of 2 rows×48 columns, which has a comb-like support section 70 which supports two rows of the applying components 69 comprising the arm section 67 and the retention tip 68. Sixteen matrix-like applicators 71 arranged in parallel, correspond to the matrix-like applicator of 32 rows×48 columns.

As shown in FIGS. 7(b) and 7(c), the matrix-like applicators 71 are arranged so that the interval between the adjoining matrix-like applicators 71 can insert the comb-like support section 70 in the gap between adjoining rollers 73 with which the base feeder 72 configures the string-like base 6 and adjoining string-like bases 6. Moreover, the interval between the retention tips 68 of the one applying component 69 is the interval between the rows that the corresponding string-like base 6 adjoins, and consequently the distance between the adjacent wells 74 of a microplate.

According to this sample delivering device, the retention tips 68 inserted into each well 74 of a microplate are moved upwards, and drawn out of the well 74, and the retention tips 68 are raised to a height at which the upper limit of the arm section 67 does not exceed the level of the base 6. Next, the matrix-like applicator is transferred horizontally along these rows of the base 6 between the rows, and is inserted between these rows. Thereafter, samples are applied at once by moving this matrix-like applicator upward and bringing the retention tips 68 into contact with the base 6.

Furthermore, FIG. 7(d) shows a matrix-like applicator in which the applying components 69 comprising the arm section 67 and the retention tips 68 are arranged six at a time for each rows, while being supported by the comb-like supporter 70, so as to be arranged for example, in the shape of a 6 rows×48 columns matrix. By using combinations of these matrix-like applicators, the efficiency of the application work to the string-like base 6 can be increased. In this case, after once descending from the top side of the string-like base 6, this is raised so that the base 6 and the liquid are contacted.

Figure 8:
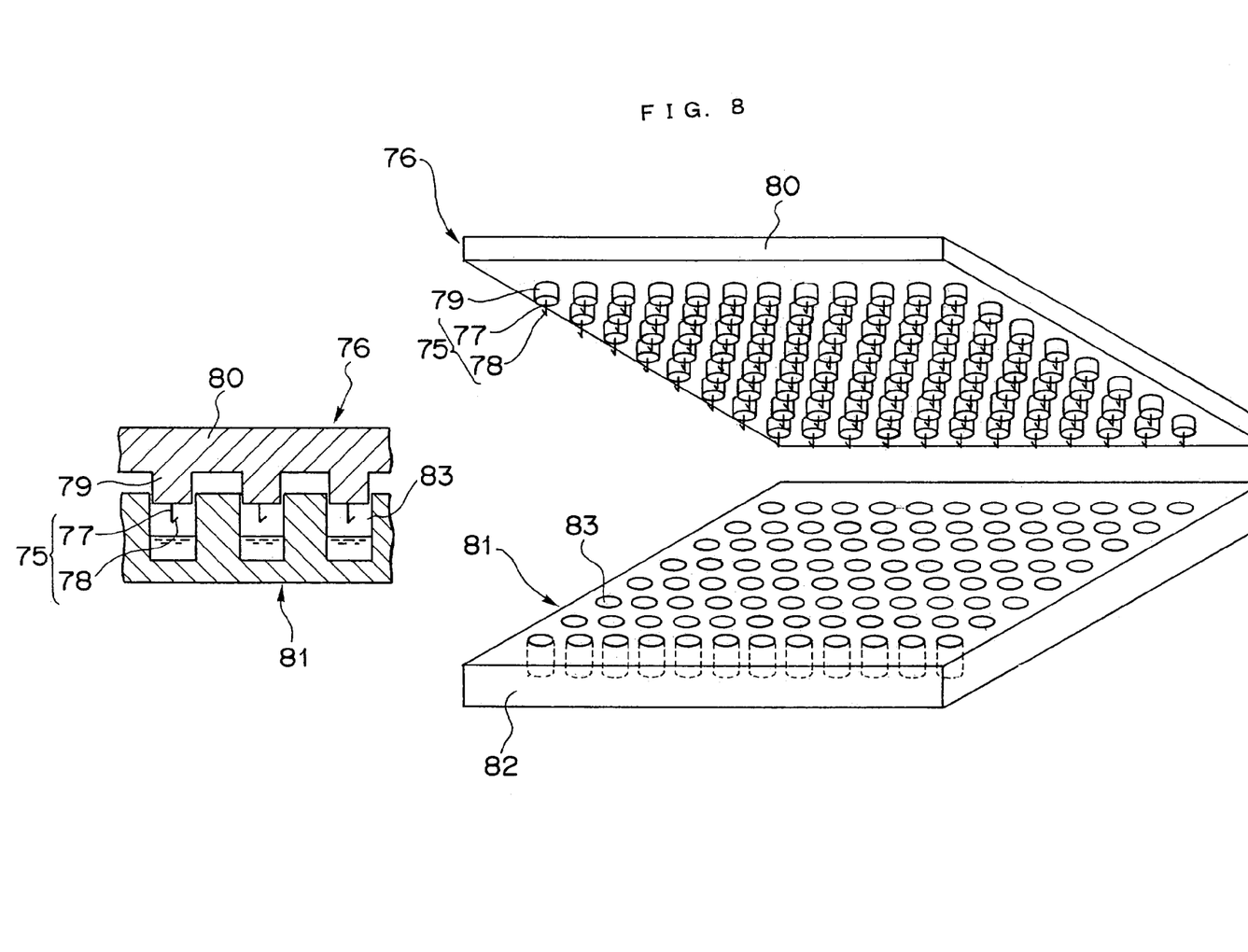
FIG. 8 is a view showing a matrix-like application section and a container according to a fourth embodiment the invention.

FIG. 8 shows a sample delivering device of a fourth embodiment.

This sample delivering device comprises a matrix-like applicator 76 in which two or more application components 75 are arranged in the shape of a matrix of 8 rows×12 columns. Each applying component 75 comprises an arm section 77 and a retention tip 78, and is mounted in a plate-like support section 80 through a lid part 79. Each lid part 79 mounted in this matrix-like applicator 76 fits all at once into each well 83 arranged in the shape of a 8 rows×12 columns matrix which is drilled in a base 82 of a separately arranged microplate 81, so as to seal the wells 83 of the microplate 81.

When each lid part 79 is made to fit into the opening of each well 83 and each well 83 is sealed, the retention tip 78 of each applying component 75 mounted below the lid part 79 is formed so as to be in a state where it does not contact with but approaches to the bottom of the well 83.

Therefore, if a solution is accommodated in each well 83 of the microplate 81, the retention tip 78 is in the state where it is dipped into the liquid in the microplate 81.

In using the matrix-like applicator 76 of the present embodiment, a suspension of a predetermined quantity which contains a sample consisting of various kinds of DNA, is accommodated in each well 83 of the microplate 81, beforehand. Next, in a condition where a reagent necessary for the PCR method, for example, a DNA polymerase etc., is beforehand retained at each retention tip 78 of the matrix-like applicator 76, the matrix-like applicator 76 is laid onto the microplate 81 so that each applying component 75 fits into and seals each well 83.

In this state, according to the PCR method, the DNA is amplified by maintaining a homiothermal condition at a predetermined temperature in the microplate 81. When amplification of the DNA is finished, the matrix-like applicator 76 is detached from the microplate 81, and processing for fixing each of the DNAs to the thin and slender base by the above-mentioned method can then be performed.

According to this embodiment, distribution of samples such as DNA to each applicator can be performed efficiently, quickly, and with high reliability. Moreover, since each well of the microplate can be sealed by each lid part, evaporation of the liquid in each well can be prevented.

Figure 9:
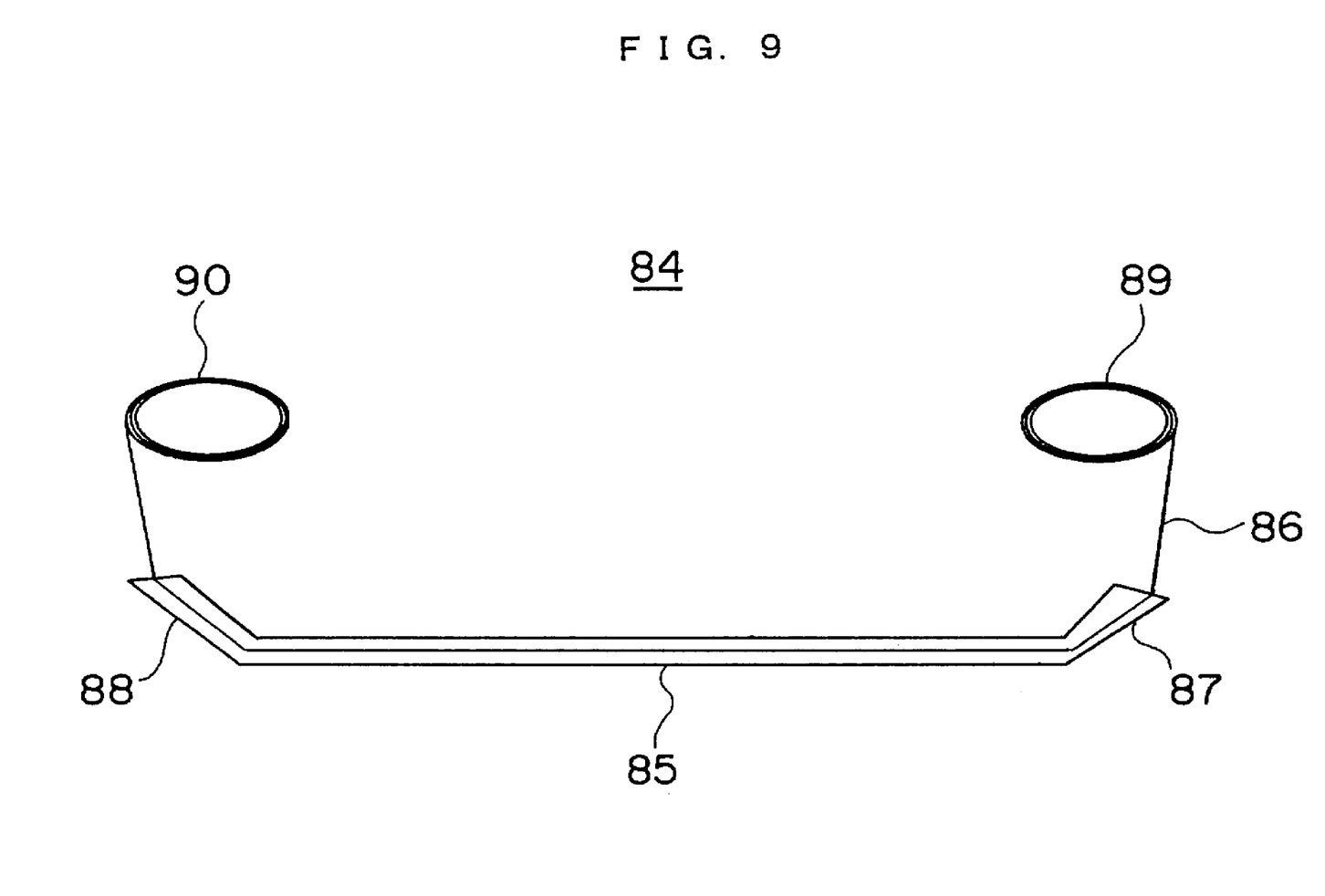
FIG. 9 is a view showing a base activation device according to a fifth embodiment the invention

A base activation device 84 of the fifth embodiment is explained on the basis of FIG. 9.

The base activation device 84 activates the base, and promotes reactions of each of the samples which should be fixed to this base.

As shown in FIG. 9, the base activation device 84 comprises a glass tube 85 capable of being threaded by a string-like base 86, a feeder for arranging and tensioning the base 86 along a path, which is not shown in the drawings, and a running driver for driving the feeder to move the base 86 through the glass tube 85.

The glass tube 85 is shaped so that the opposite ends 86 and 87 thereof are curved upwardly in a manner that a solution for activation can be accommodated within the glass tube 85. Therefore, when the string-like base 86 passes through the glass tube 85 from one reel 89 to the other reel 90, in a manner that it is tensioned, the base activation device 84 can prevent tangling of the base 86 and can keep the base 86 dipped in a solution, for a long time. Furthermore, by mounting the base activation device 84 immediately before the take-up reel 23, activated string-like base can be supplied.

The device 84 activates the carboxyl group (COOH—) or its derivative, when a carboxyl group or its derivative at the surface of the base 86 reacts with an amino group in nuclei acid. As the reagent for activation, there are carbodiimides such as EDAC (1-ethyl-3-(3-dimethylaminopropyl) carbodiimide), hydroxyimides etc. or water-soluble dehydration condensation agents, such as a chloride. By using such reagents for activation, activation is possible. The length of the glass tube 85 is 120 cm, for example. The base 86 stays in the solution EDAC for 5 minutes to react the carboxyl group or its derivative. Thereafter, the base 86 is processed for 15 minutes by adding water or a buffer solution (for example, sodium-bicarbonate buffer solution (Ph8.4)), so that an activated carboxyl group and the amino group included in the nuclei acid to be fixed are made to react Subsequently, by adding a PBS buffer solution including 1% casein, the residual activated carboxyl group is blocked.

The embodiments above have been described in detail to further explain the present invention, but in no way preclude other embodiments. Consequently, the embodiments can be altered provided the gist of the invention is retained. For example, the shape of each applying component consists of a retention tip and an arm section is not restricted to one tapering linearly downward. For example, the shape of the applying component may be one which tapers downward in a curve.

Moreover, regarding the shape of the base, this is not necessarily restricted to a long and slender shape. For example, a plane-like base can be used. The shape of the comb-like applicator and the matrix-like applicator, and the number of the rows and columns are not restricted to the above-mentioned description.

Apparatus, constituents, components, or substances, for example, the arm section, retention tip, applicator, base, base feeder, comb-like applicator, matrix-like applicator, or transfer means can be combined arbitrarily while modifying appropriately. Further, for example, it is also possible to combine any one of the samples delivering devices and the base activation device of the above-mentioned various kinds.

The invention claimed is:

1. A samples delivering device comprising:
    a base having a long and slender thread shape, at least one set of vessels having a positional arrangement relative to each other and capable of accommodating fluids containing predetermined samples to be delivered to said base,
    a samples supply section comprising a samples applicator comprising two or more retention tips capable of retaining a small quantity of fluids by being dipped in respective said fluids accommodated in respective said vessels, said two or more retention tips being positionally arranged relative to each other according to the positional arrangement of said vessels, and
    a base feeder for arranging and tensioning the base along a path determined according to the arrangement of said two or more retention tips so that contact between said base and said fluids retained by said two or more retention tips is permitted,
    wherein relative movement between said applicator and said vessels is permitted,
    wherein relative movement between said applicator and said base is permitted, and
    wherein each of said retention tips extends in a manner so that said contact between said base and said fluids retained by said two or more retention tips is effected by moving said two or more retention tips upwardly and/or transversely towards said base.

2. The samples delivering device according to claim 1, wherein said samples applicator is dismountably fitted to said sample supply section.

3. The samples delivering device according to claim 1 or claim 2, further comprising a running driver for running the base along the path.

4. The samples delivering device according to claim 1 or claim 2, wherein said samples applicator is a comb-like applicator, with said retention tips arranged at predetermined intervals so as to be comb-like.

5. The samples delivering device according to claim 2, wherein said samples applicator is formed so as to be matrix-like, with said retention tips arranged at predetermined intervals so as to be matrix-like, and wherein said base is tensioned and arranged by the feeder so that said base threads its way through rows or columns of the matrix and can run in the row direction or column direction of the matrix.

6. The samples delivering device according to claim 1 or claim 2, wherein said applicator comprises two or more applying components, each applying component being made of a thin board, sheet-like member, wherein each applying component comprises:
    an arm section shaped so as to be vertically long or tapered downwardly, and a respective one of said two or more retention tips extending from said arm section, the respective one of said two or more retention tips extending upwardly and/or transversely relative to said arm section.

7. The samples delivering device according to claim 1 or claim 2, wherein said samples applicator comprises two or more applying components, each applying component being made of a thin board, sheet-like member, wherein each applying component comprises:
    an arm section shaped so as to be vertically long or tapered downwardly, and
    a respective one of said two or more retention tips extending from said arm section, the respective one of said two or more retention tips comprising a hole or a slit.

8. The samples delivering device according to claim 6, wherein each applying component further comprises a lid part capable of being fitted to an opening of at least one of said vessels in a manner that can close up said at least one of said vessels, a respective one of said two or more retention tips being mounted under the lid part so that said retention tip the respective one of said two or more retention tips is confined within said at least one of said vessels when said at least one of said vessels is closed up by said lid part.

9. The samples delivering device according to claim 3, wherein said feeder comprises gear-like rollers that have a plurality of sharp cogs in a manner that each cog comes in contact with the base at positions between delivered samples in an interval equal to or an integer interval of the delivered samples on the base.

10. The sample delivering device according to claim 1, further comprising at least one other set of vessels capable of accommodating fluids to be delivered to said base with said fluids containing said predetermined samples;

wherein relative movement between said applicator and said sets of vessels is permitted; and wherein said retention tips are capable of retaining said fluids containing said predetermined samples together with said fluids accommodated in the at least one other set of vessels for delivery to said base.

11. A method of delivering samples, comprising the steps of:
providing at least one set of vessels having a positional arrangement relative to each other and accommodating fluids containing predetermined samples,
retaining a small quantity of said fluids in two or more retention tips of a samples applicator, said two or more retention tips positionally arranged relative to each other according to the positional arrangement of said vessels, by effecting relative movement between the samples applicator and the at least one set of said vessels and dipping said retention tips into respective said fluids accommodated in respective said vessels, and
delivering the fluid retained in the retention tips to a base having a long and slender thread shape by effecting relative movement between said retention tips and said base, comprising:
moving said retention tips upwardly and/or transversely towards said base so that the fluid retained in the retention tips contacts said base;
wherein said samples applicator further comprises two or more arm sections from which respective ones of said two or more retention tips extend transversely and/or upwardly.

12. The method according to claim 11, further comprising a step of rejuvenating the samples applicator by replacing the used samples applicator with a new one.

13. The method according to claim 11, wherein said step of delivering comprises a step for running the base tensioned along a path determined according to the arrangement of said retention tips, in a manner that said base can come in contact with the fluids retained in said retention tips.

14. The method according to claim 13, wherein in said running step, said base runs along a path disposed in the direction of arrangement of said retention tips of said comb-like samples applicator.

15. The method according to claim 12, wherein in said running step, said base runs along a path disposed in the direction of rows or columns of a matrix corresponding to the arrangements of said retention tips of said matrix-like samples applicator, in a manner that said base threads its way through the rows or columns of the matrix.

16. The method according to claim 11, comprising; a step of mixing, diluting or altering the fluids in the retention tips by relatively transferring relatively said retention tips to an other one or more sets of vessels and dipping said retention tips into fluids of said vessels after said step of retaining.

17. The method of delivering samples according to claim 11, further comprising delivering at least a portion of said fluids accommodated in the at least one set of said vessels to another set of vessels by effecting relative movement between said applicator and said sets of vessels.

* * * * *